United States Patent [19]

Crapo et al.

[11] Patent Number: 5,086,024

[45] Date of Patent: Feb. 4, 1992

[54] CATALYST SYSTEM FOR POLYMERIZATION OF OLEFINS

[75] Inventors: Clark C. Crapo, Houston; Dennis B. Malpass, LaPorte, both of Tex.

[73] Assignee: Texas Alkyls, Inc., Deer Park, Tex.

[21] Appl. No.: 560,953

[22] Filed: Aug. 1, 1990

Related U.S. Application Data

[62] Division of Ser. No. 279,377, Dec. 2, 1988, Pat. No. 4,960,878.

[51] Int. Cl.$^5$ .................. C08F 4/642; C08F 4/68; C08F 4/69
[52] U.S. Cl. .................... 502/117; 502/103; 526/165
[58] Field of Search ................ 502/103, 117

[56] References Cited

U.S. PATENT DOCUMENTS

| | | | |
|---|---|---|---|
| 4,701,432 | 10/1987 | Welborn | 502/103 X |
| 4,874,734 | 10/1989 | Kioka et al. | 502/117 X |
| 4,952,540 | 8/1990 | Kioka et al. | 502/117 X |
| 5,003,095 | 3/1991 | Beard | 556/179 |

*Primary Examiner*—Patrick P. Garvin
*Attorney, Agent, or Firm*—Richard P. Fennelly; Louis A. Morris

[57] ABSTRACT

A catalyst system for the polymerization of olefins is disclosed which comprises a metallocene component, for example, organometallic coordination compounds of a Group IVB or Group VB hydrolysis products comprising methane and $C_2$ or higher alkanes, such as isobutane, n-butane or n-hexane.

15 Claims, No Drawings

CATALYST SYSTEM FOR POLYMERIZATION OF OLEFINS

This is a division of application Ser. No. 279,377 filed Dec. 2, 1988 and now U.S. Pat. No. 4,960,878.

BACKGROUND OF THE INVENTION

1. Field of the Invention

The present invention relates to the synthesis of methylaluminoxanes which are useful as cocatalysts in the homogeneous polymerization and copolymerization of olefins and/or dienes in conjunction with metallocene compounds, e.g., such Group IVB compounds as titanium, zirconium, and hafnium.

2. Description of the Prior Art

Methylaluminoxane, prepared by carefully controlled partial hydrolysis of trimethylaluminum, is useful as a cocatalyst in conjunction with certain Group IVB compounds, such as dicyclopentadienylzirconium dichloride and racemic ethylenebis(indenyl) zirconium dichloride, in the homogeneous polymerization of olefins. Such catalyst systems, discovered by W. Kaminsky, are highly efficient and have been the subject of much interest in recent patent and journal literature, including the following: U.S. Pat. Nos. 4,404,344, 4,452,199, 4,544,762, and 4,665,208; J. Poly. Sci.: Poly. Chem. Ed., Vol. 23, page 2117(1978); Angew. Chem. Intl. Ed. Engl., Vol. 15, page 630(1976) and Vol. 19, page 390(1980); Makromol. Chem., Rapid Commun., Vol. 4, page 417(1973) and Vol. 5, page 225(1984); and J. of the Amer. Chem. Soc., Vol. 106, page 6355(1984). The known schematic schemes for the synthesis of methylaluminoxane typically show one or more of the following disadvantages: long reaction times (with hydrated salts); low yields of the methylaluminoxane (50% or lower); the potential for explosions resulting from runaway reactions; low temperatures ($-10°$ C. and below) in order to obtain optimum yields; poor batch-to-batch reproducibility; the use of exotic and expensive raw materials (for example, dimethylgalliumhydroxide, as described in the Sinn et al. publication mentioned below); or the use of unusual or complicated reactors (for example, an autoclave reactor that incorporates a milling action, as described in the Sinn et al. article cited below, an ultrasonic reactor, as described in U.S. Pat. No. 4,730,071, or the use of a high speed, high shear-inducing impeller, as described in U.S. Pat. No. 4,730,072).

At a symposium given in Hamburg, West Germany, in September, 1987, H. Sinn et al. described several new methods of preparing methylaluminoxane. Results of the symposium are given in the following citation: H. W. Sinn et al., Transition Metals and Organometallics as Catalysts for Olefin Polymerization, W. O. Kaminsky et al., eds., Springer-Verlag, New York, Proceedings of an International Symposium, Hamburg, FRG, Sept. 21-24, 1987, pages 257-268. On page 259 of this publication several unexpected observations are detailed in regard to the use of ice in the synthesis of methylaluminoxanes. However, page 262 does contain a very cursory mention that tetraisobutyldialuminoxane reacts with "a repeatedly added excess" of trimethylaluminum by giving off triisobutylaluminum that is distilled out of the reactive vessel together with the excess of trimethylaluminum. The residue is said to be "an oligomeric aluminoxane". No data is provided in regard to this ill defined product nor is its performance as a cocatalyst in olefin polymerization described in the reference.

SUMMARY OF THE PRESENT INVENTION

The instant invention relates to the synthesis of methylaluminoxanes. It is possible to form methylaluminoxanes by the reaction of a tetraalkyldialuminoxane containing $C_2$ or higher alkyl groups with trimethylaluminum using an amount of trimethylaluminum which is not present in stoichiometric excess. Also, the synthesis of methylaluminoxanes can be achieved by the reaction of a trialkylaluminum compound or a tetraalkyldialuminoxane containing $C_2$ or higher alkyl groups with water to form a polyalkylaluminoxane which is then reacted with trimethylaluminum. Further, methylaluminoxanes can be synthesized by the reaction of a polyalkylaluminoxane containing $C_2$ or higher alkyl groups with trimethylaluminum and then with water. As will be appreciated by a person of ordinary skill in the art, the tetraalkyldialuminoxane and polyalkylaluminoxane can be isolated as reagents for the instant reaction or can be present in non-isolated form when aluminum alkyls are initially reacted with appropriate amounts of water to form them. It is within the spirit and scope of the instant invention to cover these various possibilities.

DETAILED DESCRIPTION OF THE PRESENT INVENTION

In accordance with the first embodiment of the present invention, methylaluminoxane is synthesized by reacting a tetraalkyldialuminoxane containing $C_2$ or higher alkyl groups (either in isolated form or as a non-isolated intermediate as earlier described) with trimethylaluminum. The tetraalkyldialuminoxane has the formula:

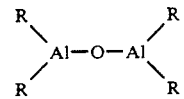

where R is the aforementioned type of alkyl group, preferably a $C_2$–$C_{20}$ alkyl group which can be either straight or branched chain or cycloalkyl including n-butyl, cyclohexyl, isobutyl, n-hexyl, and the like. The amount of trimethylaluminum used is an amount which is not in stoichiometric excess. This is unexpected in view of the above-mentioned Sinn et al. publication which only indicates, in a cursory reference, the reaction of a "repeatedly added excess of trimethylaluminum" with "tetraisobutyldialuminoxane". The molar amount of tetraalkyldialuminoxane to trimethylaluminum which can be used in accordance with the present invention ranges from about 1:0.1 to no more than 1:1. The reaction can be conducted at temperatures of from about $-10°$ C. to about $150°$ C. The reaction can be run in hydrocarbon solvent (e.g., toluene, heptane, cumene, etc.). Toluene is preferred. As would be understood by the person of ordinary skill in the art, solvents which are catalyst poisons (e.g., ethers, amines, etc.) would not be preferred materials for use.

A second embodiment of the present invention involves the synthesis of methylaluminoxanes by reacting a polyalkylaluminoxane (either in isolated or non-isolated form) with trimethylaluminum. The molar ratio of trimethylaluminum to polyalkylaluminoxane can range from about 0.1 to about 10. The polyalkylaluminoxane is of the formula:

where R is alkyl as defined above and x is an integer greater than 1, for example up to about 50. The polyalkylaluminoxane is derived from a trialkylaluminum compound or from the aforementioned tetraalkyldialuminoxane by reacting either of these materials with water under the following reaction conditions: temperatures of about $-20°$ C. to about 50° C., preferably 0°-15° C. with vigorous agitation under an inert atmosphere (e.g., nitrogen, helium, or argon). The reaction is advantageously conducted in a solvent medium, e.g., a hydrocarbon solvent. In most embodiments, evolved gases will be suitably vented to deter pressure buildup within the reactor. The molar ratio of trimethylaluminum to polyalkylaluminoxane reacted in accordance with this embodiment of the present invention to form the desired methylaluminoxane ranges from about 0.1:1 to about 10:1 on a contained aluminum molar basis. Heat should be applied after trimethylaluminum addition (e.g., refluxing, such as at 110° C. in toluene, is especially preferred in order to speed up the reaction).

A third embodiment of the present invention involves the reaction of the aforementioned polyalkylaluminoxane, which contains $C_2$ or higher hydrocarbyl, e.g., alkyl, groups, with trimethylaluminum and then with liquid water. This embodiment of the present invention is believed to involve a complex between the trimethylaluminum reagent and the polyalkylaluminoxane which is amenable to later reaction with water to form the desired methylaluminoxane reagent. The same general process as described for the second embodiment can be employed. Unlike conventional methods, reaction with liquid water is controllable and provides reproducibly a methylaluminoxane that gives high activities in olefin polymerization.

Methylaluminoxane produced by conventional methods results in an $A_s$ (specific activity units) for ethylene polymerization under standard conditions of about $1 \times 10^6$ ($A_s$=grams of polyethylene/gram Zr.hr.atm $C_2H_4$). Methylaluminoxanes produced by the first described embodiment of the instant invention showed an $A_s$ as high as $5.7 \times 10^5$ whereas the use of tetraisobutyldialuminoxane or trimethylaluminum alone, for example, showed poor polymerization activity (an $A_s$ of $10^3$ or less). The second embodiment of the instant invention has yielded $A_s$ values as high as $1.3 \times 10^6$. The third embodiment, involving precomplexation of trimethylaluminum with polyisobutylaluminoxane and subsequent reaction with water, for example, has given $A_s$ values as high as $3.7 \times 10^6$.

It has been found that the water to aluminum ratios used to make the polyalkylaluminoxane reagent have an effect on the activity ($A_s$) of the final methylaluminoxane. As is apparent from the Examples given below, for example, the highest polymerization activities, when polyisobutylaluminoxane was prepared, were achieved at $H_2O$/Al ratios for preparing the polyisobutylaluminoxane of about 0.6 to about 1.0. Polymerization activities were lower both below that range as well as above it.

The methylaluminoxane product formed by the instant process is believed to be a novel composition of matter. Conventional methylaluminoxane, when hydrolyzed, gives methane as the sole gaseous hydrolysis product due to the presence of methylaluminum species therein. In contrast, methylaluminoxanes of the instant invention, which is, in reality, a "modified" methylaluminoxane ("MMAO"), also contains alkyl substituents derived from the tetraalkyldialuminoxane and/or polyalkylaluminoxane reagents which are reacted with trimethylaluminum. Therefore, the additional presence of the aforesaid $C_2$ or higher alkyl ligands in the aluminoxane material will insure the presence of additional $C_2$+alkane hydrolysis products (either gaseous or liquid depending upon the size of the alkyl substituent): for example, isobutane, n-butane, n-hexane, and the like. The mole % methane and mole % other alkane depend on the quantity of TMAL introduced. Methane content in the hydrolysis gas typically ranges from about 20% to about 80%, though higher or lower amounts are theoretically possible. The balance is mostly alkane derived from the trialkylaluminum starting material, i.e., isobutane, n-butane, n-hexane, and the like.

Differences are also evident in comparing physical states of isolated methylaluminoxanes of the instant invention with that of conventional methylaluminoxane. Conventional methylaluminoxanes have been characterized as white solids. Methylaluminoxanes produced in accordance with the instant invention when isolated from solvent exhibit a range of physical states. Products from the first process embodiment are typically clear, colorless liquids. Products from the second embodiment range from clear, colorless liquids to white solids depending on several factors such as degree of oligomerization of the polyaluminoxane, the TMAL/IBAO ratio, and the like. Products from the third embodiment are typically clear, colorless viscous liquids. However, products from the third embodiment are likely to exhibit a range of physical states depending on the reaction conditions used during preparation, i.e., the degree of oligomerization of the polyalkylaluminoxane, the TMAL/IBAO ratio, the $H_2O$/TMAL ratio, etc.

Another distinguishing feature of the methylaluminoxanes of this disclosure is their high solubility in aliphatic hydrocarbons, such as heptane, hexane and cyclohexane. Conventional methylaluminoxanes exhibit limited solubility in such hydrocarbons.

Another aspect of the instant invention involves metallocene/aluminoxane catalysts for olefin polymerization and copolymerization and their use in such (co)polymerization processes. The instant catalyst systems differ from conventional metallocene/aluminoxane catalysts in the aluminoxane component, i.e., the use of a modified methylaluminoxane as described hereinbefore which contains $C_2$ or higher alkyl ligands in addition to methyl ligands.

The metallocene component of the instant catalyst is known and are, for example, organometallic coordination compounds of a Group IVB or Group VB metal of the Periodic Table of the Elements (56th Edition of Handbook of Chemistry and Physics, CRC Press [1975]). Included are the cyclopentadienyl derivatives (e.g., the mono-, di- and tricyclopentadienyl derivatives) of such metals as zirconium, hafnium, titanium, and vanadium. For example, cyclopentadienyl zirconium compounds of the formulae $Cp_2ZrCl_2$, $Cp_2Zr(CH_3)Cl$ and $CpZr(CH_3)_3$, where Cp stands for cyclopentadienyl can be used as the metallocene component. Other metallocene compounds which have been reported include: isopropyl (cyclopentadienyl-1-fluorenyl)hafnium; ethylenebis(4,5,6,7-tetrahydro-1-indenyl)dichlorozirconium; and ethylenebis(indenyl)dichlorozirconium. Further details in regard to this known class of metallocene compounds can be found in the following patent documents, the content of which is incorporated by reference: U.S. Pat. Nos. 4,404,344 and 4,542,199; International Patent Publication Nos. WO 87/03604, WO 88/02009, and WO 88/04672 to WO 88/04674.

The instant process and the resulting methylaluminoxane products possess a number of advantages over prior art procedures. If triisobutylaluminum (TIBAL) is selected as to form the tetraalkyldialuminoxane or polyalkylaluminoxane precursor, substantial economies may be realized since TIBAL is relatively inexpensive. Also, the critical initial reaction with TIBAL is much easier to control with the analogous reaction with trimethylaluminum thereby giving a less hazardous process. Reaction times to produce the desired methylaluminoxanes are substantially less than some prior art procedures (e.g., on the magnitude of several hours as compared to several days when hydrated salts are used as the water source). The instant process uses no "carriers" of water (e.g., hydrated salts such as aluminum sulfate or copper sulfate), thereby eliminating the need to dispose of solid by-products. The use of the relatively more expensive trimethylaluminum is made more efficient since, in most cases, there is little or no loss of insoluble methylaluminoxane species, i.e., yields are essentially quantitative. In the first two embodiments, recovery efficiencies of aluminum values charged as soluble aluminum in methylaluminoxanes typically exceed 98%. In the third embodiment, recovery efficiencies range from about 75% to essentially quantitative and are dependent on reaction parameters such as agitation rate, reaction temperature, addition rate of water, scale of experiment, etc. The reaction can be conducted at slightly above, at, or slightly below ambient temperatures eliminating or minimizing the need for extremely low temperature capability, for example, in commercial reactors. The methylaluminoxane products give olefin polymerization activities comparable, and in some cases better, than methylaluminoxane prepared by other methods. Unlike many conventional processes, the instant processes are highly reproducible and afford excellent batch-to-batch uniformity in yields and methylaluminoxane properties. Also, the resultant methylaluminoxanes from batch-to-batch perform consistently in olefin polymerization. Further, it is not necessary to isolate the methylaluminoxanes and redissolve in toluene to achieve high polymerization activities, as is the case with many conventionally prepared methylaluminoxanes.

Each of the aforementioned reactions results in the formation of a methylaluminoxane product which is believed to be different from methylaluminoxane products formed by prior art processes. Methylaluminoxanes of the present invention are useful as cocatalysts in olefin and diene polymerization and copolymerization as illustrated in the Examples which follow.

EXAMPLE 1

DIBAL-O, (tetraisobutyldialuminoxane) a commercial product of Texas Alkyls, was produced by reaction of water with triisobutylaluminum (TIBAL) in heptane using a water/TIBAL ratio of about 0.5. Solvent was stripped at 58°–65° C. under vacuum, and DIBAL-O was isolated as a clear, colorless, slightly viscous liquid. Analytical data on the isolated DIBAL-O are presented in Table I, below.

EXAMPLE 2

DIBAL-O (88.1 grams) from Example 1 was subjected to vacuum distillation conditions (<4torr) and was heated to 107° C. such that a small quantity of TIBAL (7.1 grams) was removed. The polycondensed DIBAL-O (PC DIBAL-O) was a viscous liquid that was diluted with toluene to facilitate handling. Analytical data on the polycondensed DIBAL-O in toluene are also presented in Table I.

EXAMPLES 3–6

TIBAL as a 25% solution in toluene was charged to a 300-mL flask under a nitrogen atmosphere. The flask was equipped with a magnetic stirring bar and a thermocouple to monitor the reaction temperature. Isobutylaluminoxane (IBAO) solutions were prepared by controlled addition of water to the TIBAL-containing solution in the temperature range 0°–12° C. with vigorous agitation. Water was added dropwise over a two to five hour period by syringe using a small bore needle (20 or 22 gauge). After addition of the water was completed, the clear, colorless solution of IBAO was heated to 70°–80° C. to insure substantially complete reaction and remove dissolved isobutane. Analytical data on the IBAO solutions are also summarized in Table I. In some cases, solvent was removed by distillation, and the IBAO was isolated as a viscous liquid (at $H_2O/Al$ ratios of up to about 0.7) or a white powder (at $H_2O/Al$ ratios of 0.88 and higher). Analytical data on the isolated IBAO are also given in Table I.

TABLE I

PREPARATION OR IBAO COMPOUNDS[a]

| | | | IBAO Solutions | | | Isolated IBAO | | | | |
|---|---|---|---|---|---|---|---|---|---|---|
| | | | | Hydrolysis Gas (Mole %) | | | Hydrolysis Gas (Mole %) | | | |
| Example | Product | $H_2O/Al$ | Wt % Al | Isobutane | Other[b] | Wt % Al | Isobutane | Other[b] | Molecular Weight[c] | Evolved Gas[d] |
| 1 | DIBAL-O | ≈0.5 | | | | 18.4 | 95 | 4 | 410 | 1.8 |
| 2 | PC DIBAL-O[e] | ≈0.5 | 9.7 | | | | | | | |
| 3 | IBAO | 0.98 | 3.9 | | | 26.6 | 97 | 3 | 975 | 1.2 |
| 4 | IBAO | 1.21 | | | | | | | | |
| 5 | IBAO | 1.14 | | | | | | | | |

TABLE I-continued

| | | PREPARATION OR IBAO COMPOUNDS[a] | | | | | | |
|---|---|---|---|---|---|---|---|---|
| | | | IBAO Solutions | | | Isolated IBAO | | |
| Example | Product | H$_2$O/Al | Wt % Al | Hydrolysis Gas (Mole %) | | Wt % Al | Hydrolysis Gas (Mole %) | | Molecular Weight[c] | Evolved Gas[d] |
| | | | | Isobutane | Other[b] | | Isobutane | Other[b] | | |
| 6 | IBAO | 0.88 | 3.8 | 96 | 4 | 25.8 | 90 | 10 | 951 | 1.1 |

[a]Addition required two to five hours depending on scale of experiment. Temperature at the start of the reaction was in the range of 0-12° C. As the reaction proceeded, temperature was allowed to increase to about 25° C. After the reaction was completed, the temperature was then increased to 70° C. to remove the isobutane by-product.
[b]Others include predominantly hydrogen and isobutylene and smaller amounts of propane and ethane.
[c]Cryoscopically in benzene.
[d]Expressed as moles gas per mole of aluminum.
[3]Polycondensed DIBAL-O.

EXAMPLES 7-23

Using the same equipment as in Examples 3-6, trimethylaluminum (TMAL) was added to the products of Table I, above, to produce TMAL/IBAO or TMAL/-DIBAL-O complexes. The conditions used in production of the complexes are presented in Table II, below. The TMAL/IBAO ratios in Table II are calculated by dividing molar equivalents of Al in TMAL by the molar equivalents of Al in IBAO or DIBAL-O.

TABLE II

| PREPARATION OF TMAL/IBAO COMPLEXES | | | |
|---|---|---|---|
| Example | H$_2$O/Al | TMAL/IBAO[a] | Conditions |
| 7 | 0.5 | 1 | A,E |
| 8 | 0.5 | 1 | A,F |
| 9 | 0.5 | 1 | A,C |
| 10 | 0.5 | 0.5 | A,C |
| 11 | 0.98 | 1 | B,C |
| 12 | 1.21 | 1 | B,C,G |
| 13 | 1.21 | 1 | B,C,H |
| 14 | 1.14 | 1 | B,C |
| 15 | 0.98 | 1 | B,D |
| 16 | 0.98 | 0.5 | B,D |
| 17 | 0.5 | 0.25 | A,C |
| 18 | 0.88 | 0.5 | B,D |
| 19 | 0.88 | 0.5 | B,D,I |
| 20 | 0.88 | 0.5 | B,D,J |
| 21 | 0.88 | 0.5 | B,D,K |
| 22 | 0.88 | 1.0 | B,D |
| 23 | 0.88 | 0.25 | B,C |

| | TMAL/IBAO Solutions | | | |
|---|---|---|---|---|
| | Wt % | Hydrolysis Gas (Mole %) | | |
| Example | Al | Methane | Isobutane | Other[b] |
| 7 | | | | |
| 8 | | | | |
| 9 | | | | |
| 10 | | | | |
| 11 | 7.8 | 68 | 24 | 8 |
| 12 | 4.9 | 79 | 20 | 1 |
| 13 | 6.8 | | | |
| 14 | 7.3 | 73 | 26 | 1 |
| 15 | 7.4 | 76 | 22 | 2 |
| 16 | 5.8 | 60 | 37 | 3 |
| 17 | | | | |
| 18 | 5.8 | 61 | 38 | 1 |
| 19 | 8.2 | 58 | 36 | 6 |
| 20 | 14.6 | 54 | 38 | 7 |
| 21 | | | | |
| 22 | 7.5 | 71 | 25 | 4 |
| 23 | 4.8 | 35 | 63 | 2 |

| | Isolated TMAL/IBAO | | | | |
|---|---|---|---|---|---|
| | Wt % | Hydrolysis Gas (Mole %) | | | |
| Example | Al | Methane | Isobutane | Other[b] | Molecular Weight[c] | Evolved Gas[d] |
| 7 | 24.6[e] | 60 | 38 | 3 | | |
| 8 | 23.5[e] | 62 | 36 | 2 | | |
| 9 | 23.7[e] | 60 | 38 | 2 | | |
| 10 | 21.6[e] | 47 | 50 | 2 | | |
| 11 | | | | | | |
| 12 | | | | | | |
| 13 | | | | | | |
| 14 | | | | | | |
| 15 | 33.3[f] | 64 | 29 | 7 | 788 | 1.2 |
| 16 | 19.7[f] | 28 | 66 | 6 | | |
| 17 | | | | | | |
| 18 | | | | | | |
| 19 | | | | | | |
| 20 | | | | | | |
| 21 | 34.2[f] | 58 | 29 | 13 | 4810 | 1.3 |
| 22 | | | | | | |
| 23 | | | | | | |

CONDITIONS:
A - Neat TMAL and neat commercial DIBAL-O.
B - Toluene solutions.
C - IBAO/TMAL heated to 60-85° C. for one hour.
D - IBAO/TMAL/toluene refluxed at 110° C. for one to three hours.
E - Concentrated by distillation of aluminum alkyl.
F - No heat.
G - Two-phase system obtained; analysis is of supernatant only.
H - Two-phase system obtained; analysis is for total sample, i.e., supernatant plus gelatinous lower phase.
I - Solvent removed via distillation resulting in a 25% reduction in volume of sample.
J - Solvent removed via distillation resulting in a 50% reduction in volume of sample.
K - Solvent removed to isolate solid TMAL/IBAO (0.88) = 0.5

[a]Ratio of moles Al in TMAL to moles Al in IBAO.
[b]Others include predominantly hydrogen and small amounts of propane, isobutylene and ethane.
[c]Cryoscopically in benzene.
[d]Expressed as moles gas per mole of aluminum.
[e]Isolated product was a clear colorless liquid.
[f]Isolated product was a white solid.

EXAMPLES 24-47

Products of examples in Table II, above, were used in a standard ethylene polymerization test in a 1-L Autoclave Engineers Zipperclave reactor. Data are compiled in Table III below. The procedure was as follows. High purity, dry toluene (500 mL) was degassed with nitrogen and was charged to the vessel. Using a syringe assembly, the various cocatalyst samples produced in Examples 7-23 were charged such that a total of $4 \times 10^{-3}$ mole of aluminum was introduced. A dilute toluene solution of zirconocene dichloride ($6 \times 10^{-8}$ to $4 \times 10^{-7}$ mole) was then charged to the vessel. The contents were then heated to 90° C. ±2° C. unless otherwise noted. Ethylene (150 psig) was introduced to the autoclave while stirring the reactor contents at 1000 rpm. After 15 minutes, polymerization was terminated by blocking the flow of ethylene with subsequent venting and cooling of the vessel. Polyethylene was isolated as a white powder or a white fibrous material. The melt index (MI) and high load melt index (HLMI) were measured using ASTM D-1238, Conditions E and F. The melt index ratio is obtained by dividing HLMI by MI and is considered a measure of the molecular weight distribution (MWD). A low MIR indicates a narrow MWD.

TABLE III
ETHYLENE POLYMERIZATIONS WITH MODIFIED METHYLALUMINOXANE (MMAO) AND ZIRCONOCENE DICHLORIDE[a]

| Example | Aluminoxane Cocatalyst | MMAO Source (Example) | Specific Activity ($\times 10^3$) |
|---|---|---|---|
| 24 | DIBAL-O | 1 | 4.1 |
| 25 | PC DIBAL-O/Toluene | 2 | 6.1 |
| 26 | TMAL/DIBAL-O = 1 | 7 | 110 |
| 27 | TMAL/DIBAL-O = 1 | 7 | 250 |
| 28 | TMAL/DIBAL-O = 1 | 7 | 570 |
| 29 | TMAL/DIBAL-O = 1 | 8 | 18 |
| 30 | TMAL/DIBAL-O = 1 | 9 | 270 |
| 31 | TMAL/DIBAL-O = 0.5 | 10 | 200 |
| 32 | TMAL/Toluene | | Trace |
| 33 | IBAO (0.98) | 3 | 4.2 |
| 34 | TMAL/IBAO (0.98) = 1 | 11 | 96 |
| 35 | TMAL/IBAO (1.21) = 1 | 12 | 2.5 |
| 36 | TMAL/IBAO (1.21) = 1 | 13 | 1.4 |
| 37 | TMAL/IBAO (1.14) = 1 | 14 | 2.6 |
| 38 | TMAL/IBAO (0.98) = 1 | 15 | 110 |
| 39 | TMAL/IBAO (0.98) = 0.5 | 16 | 140 |
| 40 | TMAL/DIBAL-O = 0.25 | 17 | 23 |
| 41 | TMAL/IBAO (0.88) = 0.5 | 18 | 670 |
| 42 | TMAL/IBAO (0.88) = 0.5 | 19 | 920 |
| 43 | TMAL/IBAO (0.88) = 0.5 | 20 | 930 |
| 44 | IBAO (0.88) | 6 | 7.7 |
| 45 | MAO/Toluene[c] | | 1000 |
| 46 | TMAL/IBAO (0.88) = 1.0 | 22 | 670 |
| 47 | TMAL/IBAO (0.88) = 0.25 | 23 | 93 |

| Example | Aluminoxane Cocatalyst | Melt Index | Melt Index Ratio | Comments |
|---|---|---|---|---|
| 24 | DIBAL-O | | | Control |
| 25 | PC DIBAL-O/Toluene | | | Control |
| 26 | TMAL/DIBAL-O = 1 | 2.3 | 16 | |
| 27 | TMAL/DIBAL-O = 1 | 1.3 | 16 | 86–96° C. |
| 28 | TMAL/DIBAL-O = 1 | 0.4 | 16 | |
| 29 | TMAL/DIBAL-O = 1 | | | |
| 30 | TMAL/DIBAL-O = 1 | | | |
| 31 | TMAL/DIBAL-O = 0.5 | | | |
| 32 | TMAL/Toluene | | | Control |
| 33 | IBAO (0.98) | | | Control |
| 34 | TMAL/IBAO (0.98) = 1 | | | |
| 35 | TMAL/IBAO (1.21) = 1 | | | |
| 36 | TMAL/IBAO (1.21) = 1 | | | |
| 37 | TMAL/IBAO (1.14) = 1 | | | |
| 38 | TMAL/IBAO (0.98) = 1 | 0.5 | 25 | |
| 39 | TMAL/IBAO (0.98) = 0.5 | 0.5 | 20 | |
| 40 | TMAL/DIBAL-O = 0.25 | | | |
| 41 | TMAL/IBAO (0.88) = 0.5 | 0.4 | 15 | |
| 42 | TMAL/IBAO (0.88) = 0.5 | 0.4 | 15 | |
| 43 | TMAL/IBAO (0.88) = 0.5 | 0.5 | 16 | |
| 44 | IBAO (0.88) | | | Control |
| 45 | MAO/Toluene[c] | 0.2 | 15 | Control |
| 46 | TMAL/IBAO (0.88) = 1.0 | 0.3 | 17 | |
| 47 | TMAL/IBAO (0.88) = 0.25 | | | |

[a]Ethylene polymerizations were conducted using zirconocene dichloride at 150 psig of ethylene at 90° C. ± 2 for 15 minutes unless otherwise noted.
[b]gPE/(gZr.atmC$_2$H$_4$.hr).
[c]MAO produced via reaction of TMAL with Al(OH)$_3$.xH$_2$O as described in U.S. Ser. No. 112,341, filed October 26, 1987.

EXAMPLES 48-51

IBAO with a H$_2$O/Al ratio of 0.88±0.01 was prepared in toluene solution as described in Examples 3-6. TMAL was then added, and the mixture was heated to 70°–85° C. for one hour. The product was then cooled, and water was added slowly by syringe using a small bore needle over a period of 20 minutes while stirring vigorously and controlling the temperature in the range of 0°–10° C. The reaction proceeded controllably with little or no solids or gel formation. Recovery efficiencies of aluminum values charged as soluble aluminum in the methylaluminoxane solutions in Examples 48, 50 and 51 were 93.3%, 99.5%, and 98.8%, respectively. The resultant MMAO products were tested in ethylene polymerization, described as before, and the resulting data are presented in Table IV, below.

TABLE IV
ETHYLENE POLYMERIZATIONS USING MMAO VIA TMAL/IBAO/H$_2$O[a]

| | Reactants | |
|---|---|---|
| Example | TMAL/IBAO | H$_2$O/TMAL |
| 48 | TMAL/IBAO (0.89) = 0.5 | 0.52 |
| 49 | TMAL/IBAO (0.89) = 0.5 | 0.89 |
| 50 | TMAL/IBAO (0.88) = 0.5 | 0.31 |
| 51 | TMAL/IBAO (0.88) = 1.0 | 0.32 |

| | MMAO from TMAL/IBAO/H$_2$O | | | |
|---|---|---|---|---|
| | Wt % | Hydrolysis Gas (Mole %) | | |
| Example | Al | Methane | Isobutane | Others[b] |
| 48 | 2.3 | 46 | 51 | 3 |
| 49 | 2.3 | 46 | 53 | 1 |
| 50 | 5.4 | 46 | 52 | 2 |
| 51 | 7.7 | 64 | 32 | 4 |

| Example | Specific Activity[c] ($\times 10^3$) | Melt Index | Melt Index Ratio | Comments |
|---|---|---|---|---|
| 48 | 180 | | | |
| 49 | 9.6 | | | |
| 50 | 330 | 0.5 | 15 | A$_s$ of TMAL/IBAO (0.88) = 0.5 before H$_2$O addition was 240 $\times 10^3$ |
| 51 | 1200 | 0.4 | 17 | A$_s$ of TMAL/IBAO (0.88) = 1.0 before H$_2$O addition was 670 $\times 10^3$ |

[a]Ethylene polymerizations were conducted using zirconocene dichloride at 150 psig of ethylene at 90° C. ± 2 for 15 minutes unless otherwise noted.
[b]Others include predominantly hydrogen and smaller amounts of propane, isobutylene and ethane.
[c]gPE/(gZr.atmC$_2$H$_4$.hr).

EXAMPLE 52

TIBAL as a 25% solution in toluene (246.4 grams of solution containing 3.40% Al) was charged to a flask equipped as described in Example 3-6. An IBAO was then prepared by addition of 3.92 grams of water (H$_2$O/Al=0.70) via syringe over a 30-minute period while controlling temperature between 0° C. and 5° C. The clear, colorless IBAO solution was then heated to 75° C. to insure complete reaction and to drive off dissolved isobutane. A sample of the IBAO solution was then removed for analysis and showed 3.7% Al and the hydrolysis gas composition was >98 mole % isobutane. This IBAO solution was used in Examples 53 and 54 to produce TMAL/IBAO.

A portion of the above IBAO solution was used to isolate solvent-free IBAO. Toluene solvent was removed by vacuum-stripping and mild heating ($\leq 60°$ C.). IBAO (H$_2$O/Al=0.70) was isolated as a clear, colorless but viscous liquid with the following analytical values: 20.8% Al and 97% isobutane in hydrolysis gas, and the evolved gas analysis showed 1.4 mole of gas per g-atom of aluminum. The molecular weight of the IBAO (cryoscopically in benzene) was 447.

EXAMPLE 53

To 90.0 grams of the IBAO solution (3.7% Al) prepared in Example 52 was added 8.80 grams of TMAL giving a TMAL/IBAO ratio of 1.0. The resulting solution was heated to reflux for 60 minutes. Analysis of the TMAL/IBAO solution showed 6.8% Al and the hydrolysis gas composition showed 33 mole % isobutane and 63 mole % methane.

EXAMPLE 54

The same procedure as described in Example 53 was followed except 107 gram s of IBAO solution from Example 52 and 5.22 grams of TMAL were charged to achieve TMAL/IBAO=0.5. The resultant TMAL/IBAO solution showed 5.7% Al and 48% methane, and 44% isobutane in the hydrolysis gas.

EXAMPLE 55

To 86.5 grams of toluene solution of TMAL/IBAO from Example 53 was added 0.61 grams of $H_2O$ ($H_2O$/TMAL=0.31) with vigorous agitation over a 40-minute period keeping temperature between 0° C. and 12° C. The product was subsequently refluxed for 60 minutes. The resultant product showed a very small (<1 mL) lower gelatinous phase and a larger clear, colorless liquid. The product was shaken vigorously to suspend the small lower phase and an analysis of the total sample showed 6.9% Al and the hydrolysis gas composition showed 30% isobutane and 65% methane.

EXAMPLE 56

Another IBAO solution was prepared as in Example 52 with 242 grams of TIBAL/toluene solution and 3.84 grams of $H_2O$ ($H_2O$/Al=0.70). A sample was analyzed and showed 3.7% Al. The hydrolysis gas composition was 94% isobutane. This experiment shows excellent reproducibility of results compared to Example 52.

EXAMPLE 57

A TMAL/IBAO=1 was prepared as in Example 53 by reaction of 180.8 grams of IBAO solution from Example 56 and 7.6 grams TMAL. Analysis showed 6.9% Al and the hydrolysis gas showed 29 mole % isobutane and 66% methane. This experiment shows excellent reproducibility of TMAL/IBAO preparation compared to Example 53.

A similar but independent preparation of a TMAL/IBAO (0.70)=1.0 was conducted using IBAO from Example 52. The solvent was removed via mild heating and application of vacuum affording a clear, colorless liquid. The distillate contained 2.0% aluminum indicating some removal of volatile aluminum alkyl (mostly TMAL) with the toluene. Analysis of the isolated liquid product (still pot residue) showed 25.7% Al and the hydrolysis gas showed 53% methane and 43% isobutane. (This liquid product, when used in ethylene polymerization, showed an $A_s$ of $1.2 \times 10^6$ which is in good agreement with the product of Example 53 and the product of the first paragraph of this Example 57). The molecular weight of the isolated product was determined to be 385 (cryoscopically in benzene). An evolved gas analysis showed 2.0 moles of gas per g-atom of aluminum.

EXAMPLE 58

The procedure of Example 55 was followed except to 89.2 grams of TMAL/IBAO (0.70)=1 from Example 57 only 0.33 gram of $H_2O$ was added ($H_2O$/TMAL=0.16). A small lower phase (<1 mL) was observed and analysis of the total sample showed 6.9% Al and 63% methane, and 31% isobutane in the hydrolysis gas.

EXAMPLE 59

The procedure of Example 55 was followed except to 67.9 grams of TMAL/IBAO from Example 57 was added 0.78 grams of $H_2O$ ($H_2O$/TMAL=0.50). A small lower phase (<1 mL) was again observed. Analysis of the total sample showed 7.0% Al and 64% methane, and 33% isobutane in the hydrolysis gas.

EXAMPLE 60

Another preparation of TMAL/IBAO was made following the general procedure described in Examples 52 and 56 except on a larger scale. Thus, to 1501.7 grams of a 25% solution of TIBAL in toluene in a 3-L flask was added 23.8 grams of $H_2O$ ($H_2O$/Al=0.7). Product solution was then heated to 70°-80° C. for about 30 minutes to drive off isobutane. TMAL (146.3 grams) was then added (TMAL/IBAO - 1.0) and the product refluxed for one hour. To the solution was added 18.3 grams of $H_2O$ by the procedure described in Example 55. After addition of water, the solution was maintained at room temperature with stirring for 16 hours, then heated to reflux for 1½ hours. A lower gelatinous phase formed during water addition to the TMAL/IBAO solution possibly owing to less effective agitation in the larger flask. However, after standing overnight, 1183 grams of clear, colorless product was isolated by decantation which analysis showed to contain 6.9% Al and 65% methane, and 28% isobutane in the hydrolysis gas. The efficiency based on aluminum recovered was 78%.

EXAMPLES 61-67

Products from Examples 53-60 were evaluated in ethylene polymerization as before except only $1 \times 10^{-8}$ to $6 \times 10^{-8}$ moles of zirconocene dichloride were used. Results are compiled in Table 5.

Note that independently prepared MMAO from Examples 53 and 57 showed good agreement in ethylene polymerization ($A_s = 1.1 \times 10^6$ and $1.3 \times 10^6$, respectively). Note further that those TMAL/IBAO solutions to which water was added (Examples 55, 58 and 59) were more efficient cocatalysts in ethylene polymerization than the TMAL/IBAO starting materials. Note also that the scale-up product from Example 60 showed activity comparable to product from Examples 55, 58 and 59.

TABLE V

ETHYLENE POLYMERIZATION WITH MMAO

| Example | MMAO Source | Moles Zr | Specific Activity ($10^3$) | Melt Index | Melt Index Ratio |
|---|---|---|---|---|---|
| 61 | Example 53 | $6 \times 10^{-8}$ | 1100 | 0.4 | 14 |
| 62 | Example 54 | $6 \times 10^{-8}$ | 730 | 0.7 | 14 |
| 63 | Example 55 | $1 \times 10^{-8}$ | 2200 | 0.4 | 14 |
| 64 | Example 57 | $6 \times 10^{-8}$ | 1300 | 0.5 | 14 |
| 65 | Example 58 | $2 \times 10^{-8}$ | 3100 | 0.3 | 15 |
| 66 | Example 59 | $1 \times 10^{-8}$ | 3700 | 0.4 | 11 |
| 67 | Example 60 | $2 \times 10^{-8}$ | 3400 | 0.5 | 14 |

EXAMPLE 68

Tri-n-hexylaluminum (TNHAL) (52.7 grams) was mixed with 98 grams of toluene. An n-hexylaluminoxane (NHAO) was then prepared by addition of 2.36 grams of water ($H_2O/Al=0.70$). The temperature was controlled between 0° and 10° C. The clear, colorless solution was then heated to 80° C. to insure complete reaction. A sample of the solution was analyzed and showed 3.5% Al and the hydrolysis product was 97% hexane.

EXAMPLE 69

To 104.4 grams of the NHAO solution prepared in Example 70 was added 9.2 grams of TMAL giving a TMAL/NHAO ratio of 1.0. The resulting solution was heated to 96° C. for 1½ hours. Analysis of the TMAL/NHAO solution showed 6.0% Al.

EXAMPLE 70

To 34.5 grams of tri-n-butylaluminum (TNBAL) (13.4% Al) was added 98.4 grams of toluene. The solution was cooled and maintained at 0°-10° C. while 2.19 grams of water were added over a 60-minute period. The solution was then heated to 85° C. to remove butane. The solution was treated with 12.6 grams of TMAL and heated to 110° C. for 90 minutes. Analysis of the TMAL/NBAO solution showed 6.9% Al and the hydrolysis gas composition showed 33% n-butane and 66% methane.

EXAMPLE 71

To 97.4 grams of TMAL/NBAO solution (6.9% Al) prepared in Example 72 was added 0.67 grams of water ($H_2O/Al=0.3$) while maintaining the temperature at 0°-5° C. The resultant solution was heated to 90° C. Analysis of the product showed 6.9% Al and the hydrolysis gas composition showed 34% n-butane and 65% methane.

EXAMPLES 72-74

Polymerization of ethylene was performed as before with product from Examples 69-71. Results are presented in the table below.

TABLE VI
ETHYLENE POLYMERIZATION WITH MMAO

| Example | MMAO Source | Moles Zr | Specific Activity ($10^3$) | Melt Index | Melt Index Ratio |
|---|---|---|---|---|---|
| 72 | Example 69 | $4 \times 10^{-7}$ | 67 | — | — |
| 73 | Example 70 | $1 \times 10^{-7}$ | 270 | 1.0 | 14 |
| 74 | Example 71 | $1 \times 10^{-7}$ | 250 | 0.5 | 28 |

EXAMPLE 75

From the preparation in Example 60, a 169.0 gram portion was stripped of toluene using controlled vacuum at 60°-70° C. A clear, colorless viscous liquid was obtained. Analysis showed the isolated product to contain 29.5% Al and 56% methane and 37% isobutane in the hydrolysis gas. The molecular weight was determined to be 670 (cryoscopically in benzene). An evolved gas analysis showed 1.7 moles of gas per g-atom of aluminum.

To 1.37 gram of isolated product, 6.45 grams of toluene was added and the resultant solution was used in polymerization. Specific activity of the reconstituted product was $2.2 \times 10^6$. This activity is in reasonable agreement with that observed ($3.4 \times 10^6$) with the solution prepared in Example 60.

The foregoing Examples are set forth for illustrative reasons only and should not be construed in a limiting context. The scope of protection that is sought is set forth in the claims which follow.

We claim:

1. A catalyst system for the polymerization of olefins which comprises a metallocene component and a methylaluminoxane which, when hydrolyzed, evolves hydrolysis products comprising methane and $C_2$ or higher alkanes.

2. A catalyst system as claimed in claim 1 wherein the metallocene component comprises an organometallic coordination compound of a Group IVB or Group VB metal.

3. A catalyst system as claimed in claim 2 wherein the organometallic coordination compound comprises a zirconium compound.

4. A catalyst system as claimed in claim 1 wherein the $C_2$ or higher alkane hydrolysis product is selected from the group consisting of isobutane, n-butane, and n-hexane.

5. A catalyst system as claimed in claim 1 wherein the methane content from the hydrolysis ranges from about 20% to about 80%, by weight.

6. A catalyst system as claimed in claim 2 wherein the methane content from the hydrolysis ranges from about 20% to about 80%, by weight, and the $C_2$ or higher alkane hydrolysis product constitutes the remainder and is selected from the group consisting of isobutane, n-butane, and n-hexane.

7. A catalyst system as claimed in claim 1 wherein methylaluminoxane is formed by reaction of a tetraalkyldialuminoxane containing $C_2$ or higher alkyl groups with an amount of trimethylaluminum that is not in stoichiometric excess.

8. A catalyst system as claimed in claim 7 wherein the molar amount of tetraalkyldialuminoxane to trimethylaluminum ranges from about 0.1:1 to no more than 1:1 and the reaction is conducted at temperatures ranging from about −10° C. to about 150° C.

9. A catalyst system as claimed in claim 7 wherein the alkyl groups are isobutyl groups.

10. A catalyst system as claimed in claim 1 wherein the methylaluminoxane is formed by the reaction of a tetraalkyldialuminoxane containing $C_2$ or higher alkyl groups with water to form a polyalkylaluminoxane which is then reacted with trimethylaluminum.

11. A catalyst system as claimed in claim 10 wherein the alkyl groups are isobutyl groups.

12. A catalyst system as claimed in claim 1 wherein the methylaluminoxane is formed by the reaction of a polyalkylaluminoxane containing $C_2$ or higher alkyl groups with trimethylaluminum and then with water.

13. A catalyst system as claimed in claim 12 wherein the alkyl groups are isobutyl groups.

14. A catalyst system as claimed in claim 13 wherein the molar ratio of trimethylaluminum to polyalkylaluminoxane ranges from about 0.1 to about 10 at temperatures of from about −20° C. to about 50° C.

15. A catalyst system as claimed in claim 14 wherein the molar ratio of trimethylaluminum to polyalkylaluminoxane ranges from about 0.1 to about 10 at temperatures of from about −20° C. to about 50° C.

* * * * *